US007723098B2

(12) United States Patent  
Tohda et al.

(10) Patent No.: US 7,723,098 B2
(45) Date of Patent: May 25, 2010

(54) METHOD OF CONSTRUCTING HOST AND METHOD OF PRODUCING HETEROLOGOUS PROTEIN

(75) Inventors: Hideki Tohda, Kanagawa (JP); Yuko Hama, Kanagawa (JP); Hiromichi Kumagai, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 327 days.

(21) Appl. No.: 10/724,108

(22) Filed: Dec. 1, 2003

(65) Prior Publication Data

US 2004/0132192 A1 Jul. 8, 2004

Related U.S. Application Data

(63) Continuation of application No. PCT/JP02/05223, filed on May 29, 2002.

(30) Foreign Application Priority Data

May 29, 2001 (JP) .............................. 2001-160128

(51) Int. Cl.
- C12N 1/19 (2006.01)
- C12Q 1/68 (2006.01)
- C12N 15/63 (2006.01)

(52) U.S. Cl. ........................................ 435/254.2; 435/6
(58) Field of Classification Search ....................... None
See application file for complete search history.

(56) References Cited

U.S. PATENT DOCUMENTS

| 6,110,703 | A * | 8/2000 | Egel-Mitani et al. ........ 435/69.1 |
| 2003/0166179 | A1 * | 9/2003 | Rajgarhia et al. ............ 435/139 |
| 2005/0272125 | A1 * | 12/2005 | Hoeg-Jensen et al. ...... 435/69.1 |

FOREIGN PATENT DOCUMENTS

| DE | 199 41 768 A1 | 3/2001 |
| ES | 2 133 104 A1 | 8/1999 |
| JP | 2000-78978 | 3/2000 |
| JP | 2000-136199 | 5/2000 |
| JP | 2000-262284 | 9/2000 |
| WO | 92/17595 | 10/1992 |
| WO | 95/33833 | 12/1995 |
| WO | WO 00/42203 | * 7/2000 |
| WO | 01/14522 | 3/2001 |

OTHER PUBLICATIONS

Giga-Hama, Y et al. Expression system for foreign genes using the fission yeast *Schizosaccharomyces pombe*. Biotechnology and Applied Biochemistry 30:235-244, 1999.*
www.genedb.org/genedb/pombe/.*
Wood et al. The genome sequence of *Schizosaccharomyces pombe*. Nature 415: 871-880, 2002.*
Hombergh et al. *Aspergillus* as a host for heterologous protein production: the problem of proteases. Tibtech 15: 256-263, 1997.*
Angela Simeon, et al., "Vacuolar Carboxypeptidase Y of *Saccharomyces cerevisiae* is Giycosylated, Sorted and Matured in the Fission Yeast *Schizosaccharomyces pombe*", YEAST, vol. 11, No. 3. XP-002323370, 1995, pp. 271-282.
Kailash G. Sharma, et al., "Giutathione depletion leads to delayed growth stasis in *Saccharomyces cerevislae*: evidence of a partially overlapping role for thioredoxin", Curr Genet, vol. 38, No. 2, XP-002323371, Aug. 2000, pp. 71-77.
U.S. Appl. No. 12/065,285, filed Feb. 4, 2008, Idiris, et al.
U.S. Appl. No. 12/129,413, filed May 29, 2008, Hirashima, et al.

* cited by examiner

*Primary Examiner*—Michele K Joike
(74) *Attorney, Agent, or Firm*—Oblon, Spivak, McClelland, Maier & Neustadt, L.L.P.

(57) ABSTRACT

In a method of constructing a eukaryotic host microorganism for production of a heterologous protein encoded by a trangenically introduced gene, production efficiency of the heterologous protein by the transformant obtained by introducing the gene encoding the heterologous protein into the host is improved.

Part or all of the genome unnecessary or detrimental to production of the heterologous protein by the transformant in culture is deleted or inactivated.

The eukaryotic host microorganism is preferably *Schizosaccharomyces pombe*. The part of the genome of the eukaryotic host microorganism to be deleted or inactivated is preferably a gene selected from the genes associated with energy metabolism and the genes associated with proteases, such as a pyruvate decarboxylase gene, a serine protease gene, an aminopeptidase gene and a carboxypeptidase gene.

2 Claims, No Drawings

SEQUENCE LISTING

<160> NUMBER OF SEQ ID NOS: 72

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA

<400> SEQUENCE: 1
acaagcagat ctcccagtca                                              20

<210> SEQ ID NO 2
<211> LENGTH: 40
<212> TYPE: DNA
<213> ORGANISM: Artificial Sequence
<220> FEATURE:
<223> OTHER INFORMATION: Synthetic DNA

<400> SEQUENCE: 2
agccagtggg atttgtagct ttttccatgt aattgcattt                        40

<210> SEQ ID NO 3
<211> LENGTH: 40
<212> TYPE: DNA
<213> ORGANISM: Artificial Sequence
<220> FEATURE:
<223> OTHER INFORMATION: Synthetic DNA

<400> SEQUENCE: 3
aaaagtttcg tcaatatcac tttaccaagt ttgtttatgt                        40

<210> SEQ ID NO 4

-continued

```
<211> LENGTH: 19
<212> TYPE: DNA
<213> ORGANISM: Artificial Sequence
<220> FEATURE:
<223> OTHER INFORMATION: Synthetic DNA

<400> SEQUENCE: 4
gctttcgttg aaagacttg                                                19

<210> SEQ ID NO 5
<211> LENGTH: 19
<212> TYPE: DNA
<213> ORGANISM: Artificial Sequence
<220> FEATURE:
<223> OTHER INFORMATION: Synthetic DNA

<400> SEQUENCE: 5
cgtattagcg attgaactg                                                19

<210> SEQ ID NO 6
<211> LENGTH: 40
<212> TYPE: DNA
<213> ORGANISM: Artificial Sequence
<220> FEATURE:
<223> OTHER INFORMATION: Synthetic DNA

<400> SEQUENCE: 6
agccagtggg atttgtagct gctctcacaa tcaaatcgac                         40

<210> SEQ ID NO 7
<211> LENGTH: 40
<212> TYPE: DNA
<213> ORGANISM: Artificial Sequence
<220> FEATURE:
<223> OTHER INFORMATION: Synthetic DNA

<400> SEQUENCE: 7
aaaagtttcg tcaatatcac actgtatata aatctttcts                         40

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA

<400> SEQUENCE: 8
cagggaagaa cgttccaaga                                               20

<210> SEQ ID NO 9
<211> LENGTH: 18
<212> TYPE: DNA
<213> ORGANISM: Artificial Sequence
<220> FEATURE:
<223> OTHER INFORMATION: Synthetic DNA

<400> SEQUENCE: 9
ttcatctcgg acgtgtag                                                 18

<210> SEQ ID NO 10
<211> LENGTH: 40
<212> TYPE: DNA
<213> ORGANISM: Artificial Sequence
<220> FEATURE:
<223> OTHER INFORMATION: Synthetic DNA

<400> SEQUENCE: 10
```
agccagtggg atttgtagct ttaattaaat gtgtatttta          40

<210> SEQ ID NO 11
<211> LENGTH: 40
<212> TYPE: DNA
<213> ORGANISM: Artificial Sequence
<220> FEATURE:
<223> OTHER INFORMATION: Synthetic DNA

<400> SEQUENCE: 11
aaaagtttcg tcaatatcac atccttaaat aattagaaga          40

<210> SEQ ID NO 12
<211> LENGTH: 18
<212> TYPE: DNA
<213> ORGANISM: Artificial Sequence
<220> FEATURE:
<223> OTHER INFORMATION: Synthetic DNA

<400> SEQUENCE: 12
tccactttct gttgtgga                                  18

<210> SEQ ID NO 13
<211> LENGTH: 20
<212> TYPE: DNA
<213> ORGANISM: Artificial Sequence
<220> FEATURE:
<223> OTHER INFORMATION: Synthetic DNA

<400> SEQUENCE: 13
aatctgcaat cggacatcgc                                20

<210> SEQ ID NO 14
<211> LENGTH: 40
<212> TYPE: DNA
<213> ORGANISM: Artificial Sequence
<220> FEATURE:
<223> OTHER INFORMATION: Synthetic DNA

<400> SEQUENCE: 14
agccagtggg atttgtagct tgtacgtaag aaaaaaagct          40

<210> SEQ ID NO 15
<211> LENGTH: 40
<212> TYPE: DNA
<213> ORGANISM: Artificial Sequence
<220> FEATURE:
<223> OTHER INFORMATION: Synthetic DNA

<400> SEQUENCE: 15
aaaagtttcg tcaatatcac cttatttatt ttcttggcta          40

<210> SEQ ID NO 16
<211> LENGTH: 20
<212> TYPE: DNA
<213> ORGANISM: Artificial Sequence
<220> FEATURE:
<223> OTHER INFORMATION: Synthetic DNA

<400> SEQUENCE: 16
caacatgaga cttcaaccga                                20

<210> SEQ ID NO 17
<211> LENGTH: 21
<212> TYPE: DNA

```
<213> ORGANISM: Artificial Sequence
<220> FEATURE:
<223> OTHER INFORMATION: Synthetic DNA

<400> SEQUENCE: 17
ggcccattag ctatatgaga c                                              21

<210> SEQ ID NO 18
<211> LENGTH: 40
<212> TYPE: DNA
<213> ORGANISM: Artificial Sequence
<220> FEATURE:
<223> OTHER INFORMATION: Synthetic DNA

<400> SEQUENCE: 18
agccagtggg atttgtagct aatagaaaag ttacgttatt                          40

<210> SEQ ID NO 19
<211> LENGTH: 40
<212> TYPE: DNA
<213> ORGANISM: Artificial Sequence
<220> FEATURE:
<223> OTHER INFORMATION: Synthetic DNA

<400> SEQUENCE: 19
aaaagtttcg tcaatatcac tcatgccact ggaataagtg                          40

<210> SEQ ID NO 20
<211> LENGTH: 20
<212> TYPE: DNA
<213> ORGANISM: Artificial Sequence
<220> FEATURE:
<223> OTHER INFORMATION: Synthetic DNA

<400> SEQUENCE: 20
tacccaccaa cttataagcc                                                20

<210> SEQ ID NO 21
<211> LENGTH: 21
<212> TYPE: DNA
<213> ORGANISM: Artificial Sequence
<220> FEATURE:
<223> OTHER INFORMATION: Synthetic DNA

<400> SEQUENCE: 21
gactatgttg gtggagtgca a                                              21

<210> SEQ ID NO 22
<211> LENGTH: 40
<212> TYPE: DNA
<213> ORGANISM: Artificial Sequence
<220> FEATURE:
<223> OTHER INFORMATION: Synthetic DNA

<400> SEQUENCE: 22
agccagtggg atttgtagct tccaagaaag atcaataatt                          40

<210> SEQ ID NO 23
<211> LENGTH: 40
<212> TYPE: DNA
<213> ORGANISM: Artificial Sequence
<220> FEATURE:
<223> OTHER INFORMATION: Synthetic DNA

<400> SEQUENCE: 23
aaaagtttcg tcaatatcac gagttagaaa gagcagtctt                          40
```

<210> SEQ ID NO 24
<211> LENGTH: 20
<212> TYPE: DNA
<213> ORGANISM: Artificial Sequence
<220> FEATURE:
<223> OTHER INFORMATION: Synthetic DNA

<400> SEQUENCE: 24
taggcaatag tgagacctga                                              20

<210> SEQ ID NO 25
<211> LENGTH: 18
<212> TYPE: DNA
<213> ORGANISM: Artificial Sequence
<220> FEATURE:
<223> OTHER INFORMATION: Synthetic DNA

<400> SEQUENCE: 25
tcaggtgtca tcactcac                                                18

<210> SEQ ID NO 26
<211> LENGTH: 40
<212> TYPE: DNA
<213> ORGANISM: Artificial Sequence
<220> FEATURE:
<223> OTHER INFORMATION: Synthetic DNA

<400> SEQUENCE: 26
agccagtggg atttgtagct tgtcgtagtt ttagaaatta                        40

<210> SEQ ID NO 27
<211> LENGTH: 40
<212> TYPE: DNA
<213> ORGANISM: Artificial Sequence
<220> FEATURE:
<223> OTHER INFORMATION: Synthetic DNA

<400> SEQUENCE: 27
aaaagtttcg tcaatatcac gctccttttt tggatttgct                        40

<210> SEQ ID NO 28
<211> LENGTH: 24
<212> TYPE: DNA
<213> ORGANISM: Artificial Sequence
<220> FEATURE:
<223> OTHER INFORMATION: Synthetic DNA

<400> SEQUENCE: 28
cccttctaaa catactacac gttc                                         24

<210> SEQ ID NO 29
<211> LENGTH: 20
<212> TYPE: DNA
<213> ORGANISM: Artificial Sequence
<220> FEATURE:
<223> OTHER INFORMATION: Synthetic DNA

<400> SEQUENCE: 29
tctggaaaat tgctcgttag                                              20

<210> SEQ ID NO 30
<211> LENGTH: 40
<212> TYPE: DNA
<213> ORGANISM: Artificial Sequence
<220> FEATURE:

<223> OTHER INFORMATION: Synthetic DNA

<400> SEQUENCE: 30
agccagtggg atttgtagct tttttattta tgaaaggaaa　　　　　　　　　　40

<210> SEQ ID NO 31
<211> LENGTH: 40
<212> TYPE: DNA
<213> ORGANISM: Artificial Sequence
<220> FEATURE:
<223> OTHER INFORMATION: Synthetic DNA

<400> SEQUENCE: 31
aaaagtttcg tcaatatcac tttttttcc ctaatccgat　　　　　　　　　　40

<210> SEQ ID NO 32
<211> LENGTH: 18
<212> TYPE: DNA
<213> ORGANISM: Artificial Sequence
<220> FEATURE:
<223> OTHER INFORMATION: Synthetic DNA

<400> SEQUENCE: 32
tgcaagactc caatgctc　　　　　　　　　　　　　　　　　　　　　　18

<210> SEQ ID NO 33
<211> LENGTH: 18
<212> TYPE: DNA
<213> ORGANISM: Artificial Sequence
<220> FEATURE:
<223> OTHER INFORMATION: Synthetic DNA

<400> SEQUENCE: 33
tccacccttt gtccatga　　　　　　　　　　　　　　　　　　　　　　18

<210> SEQ ID NO 34
<211> LENGTH: 40
<212> TYPE: DNA
<213> ORGANISM: Artificial Sequence
<220> FEATURE:
<223> OTHER INFORMATION: Synthetic DNA

<400> SEQUENCE: 34
agccagtggg atttgtagct tggattcttt actacttata　　　　　　　　　　40

<210> SEQ ID NO 35
<211> LENGTH: 40
<212> TYPE: DNA
<213> ORGANISM: Artificial Sequence
<220> FEATURE:
<223> OTHER INFORMATION: Synthetic DNA

<400> SEQUENCE: 35
aaaagtttcg tcaatatcac gtgaatttgg taattagcaa　　　　　　　　　　40

<210> SEQ ID NO 36
<211> LENGTH: 18
<212> TYPE: DNA
<213> ORGANISM: Artificial Sequence
<220> FEATURE:
<223> OTHER INFORMATION: Synthetic DNA

<400> SEQUENCE: 36
ctggctgttc ttagtcag　　　　　　　　　　　　　　　　　　　　　　18

<210> SEQ ID NO 37
<211> LENGTH: 19
<212> TYPE: DNA
<213> ORGANISM: Artificial Sequence
<220> FEATURE:
<223> OTHER INFORMATION: Synthetic DNA

<400> SEQUENCE: 37
acgattttcc acttgtcca                                                    19

<210> SEQ ID NO 38
<211> LENGTH: 40
<212> TYPE: DNA
<213> ORGANISM: Artificial Sequence
<220> FEATURE:
<223> OTHER INFORMATION: Synthetic DNA

<400> SEQUENCE: 38
agccagtggg atttgtagct gccaagactg ttagagtcat                             40

<210> SEQ ID NO 39
<211> LENGTH: 40
<212> TYPE: DNA
<213> ORGANISM: Artificial Sequence
<220> FEATURE:
<223> OTHER INFORMATION: Synthetic DNA

<400> SEQUENCE: 39
aaaagtttcg tcaatatcac aaattttgca atacaaaaag                             40

<210> SEQ ID NO 40
<211> LENGTH: 19
<212> TYPE: DNA
<213> ORGANISM: Artificial Sequence
<220> FEATURE:
<223> OTHER INFORMATION: Synthetic DNA

<400> SEQUENCE: 40
tcaggatatc gctgtcact                                                    19

<210> SEQ ID NO 41
<211> LENGTH: 21
<212> TYPE: DNA
<213> ORGANISM: Artificial Sequence
<220> FEATURE:
<223> OTHER INFORMATION: Synthetic DNA

<400> SEQUENCE: 41
gggtactctc aagaaggatg t                                                 21

<210> SEQ ID NO 42
<211> LENGTH: 40
<212> TYPE: DNA
<213> ORGANISM: Artificial Sequence
<220> FEATURE:
<223> OTHER INFORMATION: Synthetic DNA

<400> SEQUENCE: 42
agccagtggg atttgtagct acgccttttc gtttcttttg                             40

<210> SEQ ID NO 43
<211> LENGTH: 40
<212> TYPE: DNA
<213> ORGANISM: Artificial Sequence
<220> FEATURE:
<223> OTHER INFORMATION: Synthetic DNA

<400> SEQUENCE: 43
aaaagtttcg tcaatatcac agtatatcat atattctttt            40

<210> SEQ ID NO 44
<211> LENGTH: 18
<212> TYPE: DNA
<213> ORGANISM: Artificial Sequence
<220> FEATURE:
<223> OTHER INFORMATION: Synthetic DNA

<400> SEQUENCE: 44
atccttgggt acgcgtaa            18

<210> SEQ ID NO 45
<211> LENGTH: 20
<212> TYPE: DNA
<213> ORGANISM: Artificial Sequence
<220> FEATURE:
<223> OTHER INFORMATION: Synthetic DNA

<400> SEQUENCE: 45
gttgttgatg caacggctaa            20

<210> SEQ ID NO 46
<211> LENGTH: 40
<212> TYPE: DNA
<213> ORGANISM: Artificial Sequence
<220> FEATURE:
<223> OTHER INFORMATION: Synthetic DNA

<400> SEQUENCE: 46
agccagtggg atttgtagct aaatagagtt caactatcga            40

<210> SEQ ID NO 47
<211> LENGTH: 40
<212> TYPE: DNA
<213> ORGANISM: Artificial Sequence
<220> FEATURE:
<223> OTHER INFORMATION: Synthetic DNA

<400> SEQUENCE: 47
aaaagtttcg tcaatatcac gtttcatgag tgaatgaaat            40

<210> SEQ ID NO 48
<211> LENGTH: 18
<212> TYPE: DNA
<213> ORGANISM: Artificial Sequence
<220> FEATURE:
<223> OTHER INFORMATION: Synthetic DNA

<400> SEQUENCE: 48
tatgctcata cgttccct            18

<210> SEQ ID NO 49
<211> LENGTH: 20
<212> TYPE: DNA
<213> ORGANISM: Artificial Sequence
<220> FEATURE:
<223> OTHER INFORMATION: Synthetic DNA

<400> SEQUENCE: 49
gttttgttga gatgtcttgg            20

<210> SEQ ID NO 50
<211> LENGTH: 40

<212> TYPE: DNA
<213> ORGANISM: Artificial Sequence
<220> FEATURE:
<223> OTHER INFORMATION: Synthetic DNA

<400> SEQUENCE: 50
agccagtggg atttgtagct ccaaaaaaat atattctttg                                  40

<210> SEQ ID NO 51
<211> LENGTH: 40
<212> TYPE: DNA
<213> ORGANISM: Artificial Sequence
<220> FEATURE:
<223> OTHER INFORMATION: Synthetic DNA

<400> SEQUENCE: 51
aaaagtttcg tcaatatcac attaatttta ataatacaac                                  40

<210> SEQ ID NO 52
<211> LENGTH: 20
<212> TYPE: DNA
<213> ORGANISM: Artificial Sequence
<220> FEATURE:
<223> OTHER INFORMATION: Synthetic DNA

<400> SEQUENCE: 52
gaatctcgta ttccggcatt                                                        20

<210> SEQ ID NO 53
<211> LENGTH: 18
<212> TYPE: DNA
<213> ORGANISM: Artificial Sequence
<220> FEATURE:
<223> OTHER INFORMATION: Synthetic DNA

<400> SEQUENCE: 53
cgctgtgcta atcaactg                                                          18

<210> SEQ ID NO 54
<211> LENGTH: 40
<212> TYPE: DNA
<213> ORGANISM: Artificial Sequence
<220> FEATURE:
<223> OTHER INFORMATION: Synthetic DNA

<400> SEQUENCE: 54
agccagtggg atttgtagct tttcaactat tatcagcttc                                  40

<210> SEQ ID NO 55
<211> LENGTH: 40
<212> TYPE: DNA
<213> ORGANISM: Artificial Sequence
<220> FEATURE:
<223> OTHER INFORMATION: Synthetic DNA

<400> SEQUENCE: 55
aaaagtttcg tcaatatcac tatcataagg atcgttgact                                  40

<210> SEQ ID NO 56
<211> LENGTH: 20
<212> TYPE: DNA
<213> ORGANISM: Artificial Sequence
<220> FEATURE:
<223> OTHER INFORMATION: Synthetic DNA

<400> SEQUENCE: 56
acacaatgtg gatacgaact                                          20

<210> SEQ ID NO 57
<211> LENGTH: 20
<212> TYPE: DNA
<213> ORGANISM: Artificial Sequence
<220> FEATURE:
<223> OTHER INFORMATION: Synthetic DNA

<400> SEQUENCE: 57
gttgcttgat atccgactca                                          20

<210> SEQ ID NO 58
<211> LENGTH: 40
<212> TYPE: DNA
<213> ORGANISM: Artificial Sequence
<220> FEATURE:
<223> OTHER INFORMATION: Synthetic DNA

<400> SEQUENCE: 58
agccagtggg atttgtagct tgtttaagat tgttaaatcc                    40

<210> SEQ ID NO 59
<211> LENGTH: 40
<212> TYPE: DNA
<213> ORGANISM: Artificial Sequence
<220> FEATURE:
<223> OTHER INFORMATION: Synthetic DNA

<400> SEQUENCE: 59
aaaagtttcg tcaatatcac aaaaattttt tttgtgctgg                    40

<210> SEQ ID NO 60
<211> LENGTH: 20
<212> TYPE: DNA
<213> ORGANISM: Artificial Sequence
<220> FEATURE:
<223> OTHER INFORMATION: Synthetic DNA

<400> SEQUENCE: 60
ccgttcatcg aatagctcaa                                          20

<210> SEQ ID NO 61
<211> LENGTH: 20
<212> TYPE: DNA
<213> ORGANISM: Artificial Sequence
<220> FEATURE:
<223> OTHER INFORMATION: Synthetic DNA

<400> SEQUENCE: 61
tccaaatacc agcatacgca                                          20

<210> SEQ ID NO 62
<211> LENGTH: 40
<212> TYPE: DNA
<213> ORGANISM: Artificial Sequence
<220> FEATURE:
<223> OTHER INFORMATION: Synthetic DNA

<400> SEQUENCE: 62
agccagtggg atttgtagct ataaatactt tgtcttaagg                    40

<210> SEQ ID NO 63
<211> LENGTH: 40
<212> TYPE: DNA
<213> ORGANISM: Artificial Sequence

```
<220> FEATURE:
<223> OTHER INFORMATION: Synthetic DNA

<400> SEQUENCE: 63
aaaagtttcg tcaatatcac attttgatat acccaacatg                              40

<210> SEQ ID NO 64
<211> LENGTH: 20
<212> TYPE: DNA
<213> ORGANISM: Artificial Sequence
<220> FEATURE:
<223> OTHER INFORMATION: Synthetic DNA

<400> SEQUENCE: 64
gcgccaaacg aaaagagtga                                                   20

<210> SEQ ID NO 65
<211> LENGTH: 20
<212> TYPE: DNA
<213> ORGANISM: Artificial Sequence
<220> FEATURE:
<223> OTHER INFORMATION: Synthetic DNA

<400> SEQUENCE: 65
tccatagcat gattaggcaa                                                   20

<210> SEQ ID NO 66
<211> LENGTH: 40
<212> TYPE: DNA
<213> ORGANISM: Artificial Sequence
<220> FEATURE:
<223> OTHER INFORMATION: Synthetic DNA

<400> SEQUENCE: 66
agccagtggg atttgtagct ttgagctcaa ttttttttaat                             40

<210> SEQ ID NO 67
<211> LENGTH: 40
<212> TYPE: DNA
<213> ORGANISM: Artificial Sequence
<220> FEATURE:
<223> OTHER INFORMATION: Synthetic DNA

<400> SEQUENCE: 67
aaaagtttcg tcaatatcac ttttactatt agcttaatta                              40

<210> SEQ ID NO 68
<211> LENGTH: 20
<212> TYPE: DNA
<213> ORGANISM: Artificial Sequence
<220> FEATURE:
<223> OTHER INFORMATION: Synthetic DNA

<400> SEQUENCE: 68
ttcaacagtc attgcgattg                                                   20

<210> SEQ ID NO 69
<211> LENGTH: 18
<212> TYPE: DNA
<213> ORGANISM: Artificial Sequence
<220> FEATURE:
<223> OTHER INFORMATION: Synthetic DNA

<400> SEQUENCE: 69
agcaaccgac tttgcact                                                     18
```

```
<210> SEQ ID NO 70
<211> LENGTH: 40
<212> TYPE: DNA
<213> ORGANISM: Artificial Sequence
<220> FEATURE:
<223> OTHER INFORMATION: Synthetic DNA

<400> SEQUENCE: 70
agccagtggg atttgtagct acgcattttc ttgggacttt                          40

<210> SEQ ID NO 71
<211> LENGTH: 40
<212> TYPE: DNA
<213> ORGANISM: Artificial Sequence
<220> FEATURE:
<223> OTHER INFORMATION: Synthetic DNA

<400> SEQUENCE: 71
aaaagtttcg tcaatatcac gcataatcaa ttcaagctcc                          40

<210> SEQ ID NO 72
<211> LENGTH: 18
<212> TYPE: DNA
<213> ORGANISM: Artificial Sequence
<220> FEATURE:
<223> OTHER INFORMATION: Synthetic DNA

<400> SEQUENCE: 72
cggtcattcg tttccttc                                                  18
```

METHOD OF CONSTRUCTING HOST AND METHOD OF PRODUCING HETEROLOGOUS PROTEIN

CROSS-REFERENCE TO RELATED APPLICATIONS

The present application is a continuation of PCT/JP02/05223 filed May 29, 2002 and also claims priority to JP 2001-160128 filed May 29, 2001.

TECHNICAL FIELD

The present invention relates to a eukaryotic host microorganism in which part of the genome of the eukaryotic microorganism is modified for the purpose of improving the productivity of a heterologous protein by a transformant of the eukaryotic host microorganism, a method of constructing the host, a transformant of the host and a method of producing a protein using the transformant. The eukaryotic microorganism is preferably the fission yeast, *Schizosaccharomyces pombe* (hereinafter referred to as *S. pombe*).

BACKGROUND ART

Recombinant DNA technology is used for production of heterologous proteins in various host microorganisms and animals including *Escherichia coli* (hereinafter referred to as *E. coli*). The target products are various biogenous proteins (herein, inclusive of polypeptides), and many of them have already been produced industrially for medical and other uses so far.

Among various hosts developed for production of heterologous proteins, yeasts seem favorable for expression of animal and plant proteins because of their eukaryotic similarity in the transcription and translation systems to animals and plants, and the baker's yeast (*Saccharomyces cerevisiae*) is a widely used host. Among yeasts, *S. pombe* is known to be close to animal cells in nature as is evident from the fact that it grows by fission not by budding as a result of the different evolution process it has followed since it diverged from other yeasts at early stages. Therefore, the use of *S. pombe* as the host for expression of heterologous proteins is expected to provide a gene product closer to its natural form in animal cells.

Though studies of gene expression in *S. pombe* is delayed, the recent discovery of potent promoters functional in *S. pombe* has accelerated the development of expression systems using *S. pombe* as the host, and various improvements have been added to expression vectors to develop more stable and efficient expression systems (Japanese Patent No. 2776085, JP-A-07-163373, JP-A-10-215867, JP-A-10-234375, JP-A-11-192094, JP-A-2000-136199, JP-A-2000-262284). As a result, expression systems using *S. pombe* as the host show high production efficiency now.

Production systems for heterologous proteins using eukaryotic microorganisms such as yeasts can be realized easily by conventional microbiological techniques and recombinant DNA technology with high productivity. Large cultures are already available and are acceleratingly used for actual production. Even after the scale is enlarged for actual production, cells retain the high production efficiency per cell obtained in the laboratory.

However, considering that cost reduction is often demanded in actual production, it is necessary to improve the production efficiency of heterologous proteins through improvement in cell growth efficiency, suppression of degradation of the heterologous protein of interest, more efficient eukaryotic modifications in the microorganisms or more efficient utilization of the nutrition sources. For example, increase in the conversion of the carbon sources added to the medium for culture growth into the heterologous protein of interest is expected to drastically improve cell growth efficiency and therefore production efficiency of the heterologous protein, because efficient utilization of the carbon sources in the medium for production of the heterologous protein of interest seems to be sacrificed for their consumption by metabolic systems unnecessary for cell growth or production of the heterologous protein of interest (such as the ethanol fermentation system for production of ethanol).

DISCLOSURE OF THE INVENTION

Under the above-mentioned circumstance, the present inventors studied from the above-mentioned aspects, and, as a result, found that the deletion or inactivation of part or all of the genome of the host unnecessary or detrimental to production of the heterologous protein by its transformant improves the production efficiency of the heterologous protein. The present invention aims at improvement in the production efficiency of a heterologous protein, relates to a method of constructing a eukaryotic host organism, a host constructed by the construction method, a transformant of the host obtained by introducing a gene encoding a heterologous protein into the host and a method of producing a heterologous protein using the transformant, and provides:

(1) a method of constructing a eukaryotic host microorganism for production of a heterologous protein encoded by a transgenically introduced gene, which is characterized by deleting or inactivating part or all of the genome of a eukaryotic host microorganism unnecessary or detrimental to production of the heterologous protein by a transformant of the host in culture for the purpose of improving productivity of the heterologous protein;

(2) a eukaryotic host microorganism for production of a heterologous protein encoded by a transgenically introduced gene, which is constructed by the construction method;

(3) a transformant obtained by introducing the structural gene encoding a heterologous protein into a eukaryotic host microorganism in which part or all of the genome of the eukaryotic host microorganism unnecessary or detrimental to production of the heterologous protein by the transformant in culture has been deleted or inactivated for the purpose of improving productivity of the heterologous protein; and (4) a method of producing a heterologous protein, comprising causing a transformant of a eukaryotic host microorganism having a gene encoding a heterologous protein extrinsic to the host and collecting the heterologous protein, wherein the productivity of the heterologous protein is improved by deleting or inactivating part or all of the genome of the eukaryotic host microorganism which is unnecessary or detrimental to production of the heterologous protein by the transformant in culture.

The part of the genome unnecessary or detrimental to production of the heterologous protein by the transformant in culture is preferably genes associated with energy metabolism, proteases, meiosis, transcription, cell growth and division and DNA synthesis, protein synthesis, membrane transport, cell structure maintenance, signal transduction or ion homeostasis in the eukaryotic host microorganism.

The eukaryotic microorganism is preferably a yeast, especially *S. pombe*. The part of the genome unnecessary or detrimental to production of the heterologous protein by *S. pombe* is a gene selected from the genes associated with energy metabolism (such as pyruvate decarboxylase gene) and the genes associated with proteases (such as endopeptidases like serine protease gene and exopeptidases like aminopeptidase and carboxypeptidase).

BEST MODE OF CARRYING OUT THE INVENTION

In the present invention, the eukaryotic microorganism is preferably a fungus, especially a unicellular fungus (i.e., a yeast). As the yeast, a yeast of the *Saccharomyces* genus such as the baker's yeast, a yeast of the *Schizosaccharomyces* genus or a yeast of the *Pichia* genus is preferable. Eukaryotic microorganism of the *Aspergillus* genus, the *Rhizopus* genus or the *Penicillium* genus and other eukaryotic microorganism may be mentioned. The eukaryotic microorganism particularly preferred in the present invention is a yeast of the *Schizosaccharomyces* genus, especially *S. pombe*. Hereinafter, hosts mean those eukaryotic microorganisms, unless otherwise noted.

It is common in recent years to transgenically introduce the gene encoding a protein extrinsic to a host (i.e., a heterologous protein) (hereinafter referred to as a heterologous gene) to the host and causing the host having the introduced heterologous gene (i.e., a transformant) to produce the heterologous protein and collecting the heterologous protein. While the culture of the transformant is producing the heterologous protein, part of the genome is unnecessary or detrimental to production of the heterologous protein by the transformant in culture. The part of the genome may be a gene or a nongenomic part, preferably a genomic part of the genome. Deletion or inactivation of the gene improves the production efficiency of the heterologous protein by the transformant. It is believed that a lot of such unnecessary or detrimental genes exist in a genome. Deletion or inactivation of part of these genes sufficiently meets the purpose of the present invention.

The part of the genome unnecessary or detrimental to production of the heterologous protein by the transformant may be genes essential for the wild type host to survive or grow, because such essential genes are not always necessary to a transformant culture. For example, the genes essential for conversion of carbon sources to nutrients are no longer necessary if the nutrients are added to the culture environment (culture medium). Meanwhile, in the case of yeasts which can grow not by meiosis but by budding or fission, genes associated with meiosis are not always necessary for the growth of a transformant. The existence of such unnecessary genes can be a burden to growth of the transformant or production of the heterologous protein. Therefore, deletion or inactivation of such genes lightens the burden and improves the production efficiency of the heterologous protein.

On the other hand, genes associated with proteases tend to inhibit the production of the heterologous protein. Because the heterologous protein produced is fundamentally unnecessary to the host, the transformant tends to degrade the produced heterologous protein by proteases. Since degradation of the heterologous protein is considered as a factor of reduction in the production efficiency of the heterologous protein, deletion or inactivation of the genes associated with production of such proteases improves the production efficiency of the heterologous protein.

Such genes unnecessary or detrimental to production of the heterologous protein as described above are preferably genes associated with energy metabolism, proteases, meiosis, transcription, cell growth and division and DNA synthesis, protein synthesis, membrane transport, cell structure maintenance, signal transduction or ion homeostasis. Particularly preferred are genes selected from the genes associated with energy metabolism and the genes associated with proteases.

The gene in the genes associated with energy metabolism is a gene associated with ethanol fermentation. A typical example of the genes associated with ethanol fermentation is the gene encoding pyruvate decarboxylase (the pyruvate decarboxylase gene). Deletion or inactivation of the pyruvate decarboxylase gene is considered to make the culture of the transformant distribute more energy to synthetases instead of ethanol fermentation and thereby improve the production efficiency of the heterologous protein.

The genes associated with proteases include genes encoding endopeptidases such as serine proteases, carboxyl proteases and metal proteases and exopeptidases such as aminopeptidases and carboxypeptidases. Particularly preferred are genes encoding serine proteases (serine protease genes), genes encoding aminopeptidases (aminopeptidase genes) and genes encoding carboxypeptidases (carboxypeptidase genes). Deletion or inactivation of these genes associated with proteases is considered to improve the production efficiency of the heterologous protein.

Part of the genome of the host can be deleted or inactivated by known methods. One or more parts of the genome may be deleted or inactivated. When the part to be deleted or inactivated is gene(s), deletion or inactivation a single gene or at least two genes may be effected on a single gene or two or more individual genes.

Deletion of a gene may be deletion of the entire gene or deletion of part of the gene for inactivation of the gene. Inactivation of a gene means not only deletion of part of the gene but also modification of the gene without deletion. A gene may be inactivated by inserting another gene or DNA into a certain sequence in the gene as the inactivation target. In any case, the target gene is inactivated so as to encode an inactive protein or so as to be unable to be transcribed or translated.

Though there is no restriction on the heterologous protein, it is preferably a protein which is produced by multicellular organisms such as animals and plants, especially a protein produced by a mammal (inclusive of human). Such a protein is rarely obtained with high activity by a prokaryotic host microorganism such as *E. coli* and is obtained with low production efficiency by using an animal cell line such as CHO as the host. The use of the transgenic eukaryotic host microorganism of the present invention is considered to solve these problems.

EXAMPLES

Now, the present invention will be described in further detail in reference to specific Examples.

Example 1

Improvement in the Production Efficiency of *Aequorea victria* Green Fluorescent Protein by Inactivation of the Pyruvate Decarboxylase Gene pdc1

A 1.8-kb fragment from the orotidine phosphate decarboxylase gene was inserted in the 1785-bp ORF (the protein-coding region) of the pyruvate decarboxylase gene pdc1 (SPAC1F8.07c) of the fission yeast *S. pombe* to obtain a pdc1-disrupted vector. A green fluorescent protein-producing uracil-requiring auxotroph (obtained by inactivating the orotidine phosphate decarboxylase activity of the yeast strain used in the octuplicated integrative production system disclosed in JP-A-2000-262284 through gene disruption) was transformed with the vector. A uracil-unrequiring strain capable of forming colonies on the minimum medium was collected. Analysis of the genomic DNA by PCR amplification confirmed disruption of the pyruvate decarboxylase gene.

The transformant was grown and tested for green fluorescent protein production in YPD liquid medium (1% yeast extract (DIFCO), 2% Bacto-Peptone (DIFCO), 2% glucose (Wako Pure Chemical Industries, Ltd.)) in test tube-shaped culture vessels. The production per cell was higher than in the original strain, according to fluorometry using a microplate reader (CORONA, MTP-32+MTPF2) at an excitation wavelength of 490 nm and an emission wavelength 530 nm.

Example 2

Improvement in the Production Efficiency of Aequorea victria Green Fluorescent Protein by Inactivation of the Serine Protease Gene isp6

A 1.8-kb fragment from the orotidine phosphate decarboxylase gene was inserted in the ORF (1404 bp) of a serine protease gene isp6 (SPAC4A8.04) of the fission yeast S. pombe to obtain a isp6-disrupted vector. The same uracil-requiring auxotroph as in Example 1 was transformed with the vector. A uracil-unrequiring strain capable of forming colonies on the minimum medium was collected. Analysis of the genomic DNA by PCR amplification confirmed disruption of the serine protease gene.

The transformant was grown in the same manner as in Example 1 and tested for green fluorescent protein production. The production per cell was higher than in the original strain, according to fluorometry using a microplate reader (CORONA, MTP-32+MTPF2) at an excitation wavelength of 490 nm and an emission wavelength 530 nm.

Example 3

Improvement in the Production Efficiency of Aequorea victria Green Fluorescent Protein by Inactivation of the Aminopeptidase Gene SPC4F10.02 (Aminopeptidase I)

400-hp genomic DNA sequences franking the ORE (1500 bp) of the aminopeptidase gene SPC4F10.02 (Nature 415, 871-880 (2002)) from the 5'- and 3'-sides were prepared by PCR amplification using primers having the nucleotide sequences ACAAGCAGATCTCCCAGTCA (SEQ ID NO: 1) and AGCCAGTGGGATTTGTAGCTTTTTCCATGTAATTGCATTT (SEQ ID NO: 2) and the nucleotide sequences AAAAGTTTCGTCAATATCACTTTACCAAGTTTGTTTATGT (SEQ ID NO: 3) and GCTTTCGTTGAAAGACTTG (SEQ ID NO: 4). Then, these DNA fragments were ligated with a 1.8-kbp fragment from the ura4 gene as the marker gene by PCR amplification using primers having the nucleotide sequences ACAAGCAGATCTCCCAGTCA (SEQ ID NO: 1) and GCTTTCGTTGAAAGACTTG (SEQ ID NO: 4) to give a gene disruptive vector having the ura4a gene instead of the ORE of the aminopeptidase gene in the genomic DNA sequence.

A S. pombe strain (leu1-32, -ura4-D18) was transformed with the vector. A uracil-unrequiring strain capable of forming colonies on the minimum medium was collected. Analysis of the genomic DNA using PCR amplification designed so as to amplify DNA fragments only when the intended gene was disrupted confirmed disruption of the aminopeptidase gene SPAC4F10.02.

The transformant was transformed with an expression vector obtained by inserting the Aequorea victria green fluorescent protein gene in the expression vector for fission yeast (JP-A-7-163373). After screening, the resulting transformant was incubated in YPD liquid containing 100 mg/L antibiotic G418 as the expression medium in test tube-shaped culture vessels. The production per cell was higher than in the original strain. Namely, according to fluorometry using a microplate reader (CORONA, MTP-32+MTPF2) at an excitation wavelength of 490 nm and an emission wavelength 530 nm, the expression level was increased about twice to 231, as compared with that by the non-disruptive strain containing the same gene insert.

Example 4

Improvement of the Production Efficiency of Aequorea victria Green Fluorescent Protein by Inactivation of the Carboxypeptidase SPBC16G5.09

400-hp genomic DNA sequences franking the ORE (1647 bp) of the carboxypeptidase gene SPBC16G5.09 (Nature 415, 871-880 (2002)) from the 5'- and 3'-sides were prepared by PCR amplification using primers having the nucleotide sequences CGTATTAGCGATTGAACTG (SEQ ID NO: 5) and AGCCAGTGGGATTTGTAGCTGCTCTCACAATCAAATCGAC (SEQ ID NO: 6) and the nucleotide sequences AAAAGTTTCGTCAATATCACACTGTATATAAATCTTTTCT (SEQ ID NO: 7) and CAGGGAAGAACGTTCCAAGA (SEQ ID NO: 8). Then, these DNA fragments were ligated with a 1.8-kbp fragment from the ura4 gene as the marker gene by PCR amplification using primers having the nucleotide sequences CGTATTAGCGATTGAACTG (SEQ ID NO: 5) and CAGGGAAGAACGTTCCAAGA (SEQ ID NO: 8) to give a gene disruptive vector having the ura4 gene instead of the ORF of the aminopeptidase gene in the genomic DNA sequence.

A S. pombe strain (leu1-32, ura4-D18) was transformed with the vector. A uracil-unrequiring strain capable of forming colonies on the minimum medium was collected. Analysis of the genomic DNA using PCR amplification designed so as to amplify DNA fragments only the intended gene was disrupted confirmed disruption of the carboxypeptidase SPBC16G5.09.

The transformant was transformed with an expression vector obtained by inserting the Aequorea victria green fluorescent protein gene in the expression vector for fission yeast (JP-A-7-163373). After screening, the resulting transformant was incubated in YPD liquid containing 100 mg/L antibiotic G418 as the expression medium in test tube-shaped culture vessels. The production per cell was higher than in the original strain. Namely, according to fluorometry using a microplate reader (CORONA, MTP-32+MTPF2) at an excitation wavelength of 490 nm and an emission wavelength 530 nm, the expression level was increased by about 1.6 times to 215, as compared with that by the non-disruptive strain containing the same gene insert.

Example 5

400-bp genomic DNA sequences franking the ORFs of various genes (Nature 415, 871-880 (2002)) from the 5'- and 3'-sides were prepared by PCR amplification using primers (four types A-D). Then, these DNA fragments were ligated with a 1.8-kbp fragment from the ura4 gene as the marker gene by PCR amplification using two primers (A and D of the above-mentioned four) to give gene disruptive vectors having the ura4 gene instead of the ORFs of the genes in the genomic DNA sequence. A *S. pombe* strain (leu1-32, ura4-D18) was transformed with the vectors. Uracil-unrequiring strains capable of forming colonies on the minimum medium were collected. Analysis of the genomic DNA using PCR amplification designed so as to amplify DNA fragments only when the intended genes were disrupted confirmed disruption of the intended genes.

The gene-disruptive *S. pombe* transformants were transformed with an expression vector obtained by inserting the *Aequorea victria* green fluorescent protein gene in the same manner as in Examples 3 and 4. The transformants were incubated, and the green fluorescent protein productions were measured at an excitation wavelength of 490 nm and an emission wavelength 530 nm. The absorbances were higher than those of non-disruptive strains containing the same genes insert.

The disrupted genes and the primers (4 types) used are given below.

(1)

The name of the gene: Aspertic protease gene SPCC1795.09 (putative aspartic proteinase)

The length of the ORF: 1566 bp

Primers:

```
A;    TTCATCTCGGACGTGTAG (SEQ ID NO: 9)
B;    AGCCAGTGGGATTTGTAGCTTTAATTAAATGTGTATTTTA
      (SEQ ID NO: 10)
C;    AAAAGTTTCGTCAATATCACATCCTTAAATAATTAGAAGA
      (SEQ ID NO: 11)
D;    TCCACTTTCTGTTGTGGA (SEQ ID NO: 12)
```

(2)

The name of the gene: Cytoplasmic aminopeptidase gene SPAC13A11.05 (cytosol amino peptidase)

The length of the ORF: 1542 bp

Primers:

```
A;    AATCTGCAATCGGACATCGC (SEQ ID NO: 13)
B;    AGCCAGTGGGATTTGTAGCTTGTACGTAAGAAAAAAAGCT
      (SEQ ID NO: 14)
C;    AAAAGTTTCGTCAATATCACCTTATTTATTTTCTTGGCTA
      (SEQ ID NO: 15)
D;    CAACATGAGACTTCAACCGA (SEQ ID NO: 16)
```

(3)

The name of the gene: Dipeptidyl aminopeptidase gene SPAC14C4.15c (dipeptidyl aminopeptidase)

The length of the ORF: 2606 bp

Primers:

```
A;    GGCCCATTAGCTATATGAGAC (SEQ ID NO: 17)
B;    AGCCAGTGGGATTTGTAGCTAATAGAAAAGTTACGTTATT
      (SEQ ID NO: 18)
C;    AAAAGTTTCGTCAATATCACTCATGCCACTGGAATAAGTG
      (SEQ ID NO: 19)
D;    TACCCACCAACTTATAAGCC (SEQ ID NO: 20)
```

(4)

The name of the gene: Carboxypeptidase gene SPBC337.07c (putative carboxypeptidase)

The length of the ORF: 1665 bp

Primers:

```
A;    GACTATGTTGGTGGAGTGCAA (SEQ ID NO: 21)
B;    AGCCAGTGGGATTTGTAGCTTCCAAGAAAGATCAATAATT
      (SEQ ID NO: 22)
C;    AAAAGTTTCGTCAATATCACGAGTTAGAAAGAGCAGTCTT
      (SEQ ID NO: 23)
D;    TAGGCAATAGTGAGACCTGA (SEQ ID NO: 24)
```

(5)

The name of the gene: Vacuolar carboxylase S gene SPAC24C9.08 (putative vacuolar carboxypeptidase s)

The length of the ORF: 1791 bp

Primers:

```
A;    TCAGGTGTCATCACTCAC (SEQ ID NO: 25)
B;    AGCCAGTGGGATTTGTAGCTTGTCGTAGTTTTAGAAATTA
      (SEQ ID NO: 26)
C;    AAAAGTTTCGTCAATATCACGCTCCTTTTTTGGATTTGCT
      (SEQ ID NO: 27)
D;    CCCTTCTAAACATACTACACGTTC (SEQ ID NO: 28)
```

(6)

The name of the gene: Zinc protease gene SPACUNK4.12c (putative zinc-protease)

The length of the ORF: 2910 bp

Primers:

```
A;    TCTGGAAAATTGCTCGTTAG (SEQ ID NO: 29)
B;    AGCCAGTGGGATTTGTAGCTTTTTTATTTATGAAAGGAAA
      (SEQ ID NO: 30)
C;    AAAAGTTTCGTCAATATCACTTTTTTTTCCCTAATCCGAT
      (SEQ ID NO: 31)
D;    TGCAAGACTCCAATGCTC (SEQ ID NO: 32)
```

(7)

The name of the gene: Zinc protease gene SPCC1442.07c (putative ZN-protease)

The length of the ORF: 849 bp

```
Primers:

A;      TCCACCCTTTGTCCATGA (SEQ ID NO: 33)

B;      AGCCAGTGGGATTTGTAGCTTGGATTCTTTACTACTTATA
        (SEQ ID NO: 34)

C;      AAAAGTTTCGTCAATATCACGTGAATTTGGTAATTAGCAA
        (SEQ ID NO: 35)

D;      CTGGCTGTTCTTAGTCAG (SEQ ID NO: 36)
```

(8)

The name of the gene: Metalloprotease gene SPCC965.04c (putative metallopeptidase)

The length of the ORF: 2231 bp

```
Primers:

A;      ACGATTTTCCACTTGTCCA (SEQ ID NO: 37)

B;      AGCCAGTGGGATTTGTAGCTGCCAAGACTGTTAGAGTCAT
        (SEQ ID NO: 38)

C;      AAAAGTTTCGTCAATATCACAAATTTTGCAATACAAAAAG
        (SEQ ID NO: 39)

D;      TCAGGATATCGCTGTCACT (SEQ ID NO: 40)
```

(9)

The name of the gene: Zinc metalloprotease gene SPAC17A5.04c (putative zinc metallopeptidase)

The length of the ORF: 1610 bp

```
Primers:

A;      GGGTACTCTCAAGAAGGATGT (SEQ ID NO: 41)

B;      AGCCAGTGGGATTTGTAGCTACGCCTTTTCGTTTCTTTTG
        (SEQ ID NO: 42)

C;      AAAAGTTTCGTCAATATCACAGTATATCATATATTCTTTT
        (SEQ ID NO: 43)

D;      ATCCTTGGGTACGCGTAA (SEQ ID NO: 44)
```

(10)

The name of the gene: CAAX prenyl protease I gene SPAC3H1.05 (putative CAAX prenyl protease)

The length of the ORF: 1495 bp

```
Primers:

A;      GTTGTTGATGCAACGGCTAA (SEQ ID NO: 45)

B;      AGCCAGTGGGATTTGTAGCTAAATAGAGTTCAACTATCGA
        (SEQ ID NO: 46)

C;      AAAAGTTTCGTCAATATCACGTTTCATGAGTGAATGAAAT
        (SEQ ID NO: 47)

D;      TATGCTCATACGTTCCCT (SEQ ID NO: 48)
```

(11)

The name of the gene: Dipeptidyl peptidase gene SPBC1711.12 (putative dipeptidyl peptidase)

The length of the ORF: 2052 bp

```
Primers:

A;      GTTTTGTTGAGATGTCTTGG (SEQ ID NO: 49)

B;      AGCCAGTGGGATTTGTAGCTCCAAAAAAATATATTCTTTG
        (SEQ ID NO: 50)

C;      AAAAGTTTCGTCAATATCACATTAATTTTAATAATACAAC
        (SEQ ID NO: 51)

D;      GAATCTCGTATTCCGGCATT (SEQ ID NO: 52)
```

(12)

The name of the gene: Dipeptidase gene SPCC965.12 (putative dipeptidase)

The length of the ORF: 1251 bp

```
Primers:

A;      CGCTGTGCTAATCAACTG (SEQ ID NO: 53)

B;      AGCCAGTGGGATTTGTAGCTTTTCAACTATTATCAGCTTC
        (SEQ ID NO: 54)

C;      AAAAGTTTCGTCAATATCACTATCATAAGGATCGTTGACT
        (SEQ ID NO: 55)

D;      ACACAATGTGGATACGAACT (SEQ ID NO: 56)
```

(13)

The name of the gene: Methionine metallopeptidase gene SPBC 14C8.03 (putative methionine metallopeptidase)

The length of the ORF: 1281 bp

```
Primers:

A;      GTTGCTTGATATCCGACTCA (SEQ ID NO: 57)

B;      AGCCAGTGGGATTTGTAGCTTGTTTAAGATTGTTAAATCC
        (SEQ ID NO: 58)

C;      AAAAGTTTCGTCAATATCACAAAAATTTTTTTGTGCTGG
        (SEQ ID NO: 59)

D;      CCGTTCATCGAATAGCTCAA (SEQ ID NO: 60)
```

(14)

The name of the gene: Methionine aminopeptidase gene SPBC3E7.10 (putative methionine aminopeptidase)

The length of the ORF: 1301 bp

```
Primers:

A;      TCCAAATACCAGCATACGCA (SEQ ID NO: 61)

B;      AGCCAGTGGGATTTGTAGCTATAAATACTTTGTCTTAAGG
        (SEQ ID NO: 62)
```

-continued

C;  AAAAGTTTCGTCAATATCACATTTTGATATACCCAACATG
    (SEQ ID NO: 63)

D;  GCGCCAAACGAAAAGAGTGA (SEQ ID NO: 64)

(15)

The name of the gene: Signal peptidase gene SPAC1071.04c (putative signal peptidase)

The length of the ORF: 504 bp

Primers:

A;  TCCATAGCATGATTAGGCAA (SEQ ID NO: 65)

B;  AGCCAGTGGGATTTGTAGCTTTGAGCTCAATTTTTTTAAT
    (SEQ ID NO: 66)

C;  AAAAGTTTCGTCAATATCACTTTTACTATTAGCTTAATTA
    (SEQ ID NO: 67)

D;  TTCAACAGTCATTGCGATTG (SEQ ID NO: 68)

(16)

The name of the gene: Mitochondrial processing peptidase β subunit gene SPBP23A10.15c (mitochondrial processing peptidase beta subunit)

The length of the ORF: 1374 bp

Primers:

A;  AGCAACCGACTTTGCACT (SEQ ID NO: 69)

B;  AGCCAGTGGGATTTGTAGCTACGCATTTTCTTGGGACTTT
    (SEQ ID NO: 70)

C;  AAAAGTTTCGTCAATATCACGCATAATCAATTCAAGCTCC
    (SEQ ID NO: 71)

D;  CGGTCATTCGTTTCCTTC (SEQ ID NO: 72)

INDUSTRIAL APPLICABILITY

Inactivation of the pyruvate decarboxylase gene or a protease gene in the fission yeast *S. pombe* improves production efficiency of a heterologous protein in a transformant of the fission yeast host *S. pombe*. Thus, in a protein production system using a transformant having a transgenically introduced gene encoding a heterologous protein, deletion or inactivation of part of the genome unnecessary or detrimental to production of the heterologous protein by the transformant in culture improves production efficiency of the heterologous protein.

The entire disclosure of Japanese Patent Application No. 2001-160128 filed on May 29, 2001 including specification, claims and summary is incorporated herein by reference in its entirety.

What is claimed is:

1. A method of constructing a *Schizosaccharomyces pombe* yeast cell which produces a heterologous protein, comprising
deleting or inactivating at least one *S. pombe* gene encoding enzyme selected from the group consisting of pyruvate decarboxylase pdc 1 designated SPAC 1 F8.07c and serine protease isp 6 designated SPAC4A8.04; and
transforming the *Schizosaccharomyces pombe* yeast cell with a polynucleotide which encodes the heterologous protein,
wherein the deletion or inactivation of the at least one gene results in increased production of the heterologous protein compared to a *Schizosaccharomyces pombe* yeast cell in which the at least one gene has not been deleted or inactivated.

2. A method of producing a heterologous protein, comprising constructing a *Schizosaccharomyces pombe* yeast cell in which at least one *S. pombe* gene is deleted or inactivated, wherein the at least one *S. pombe* gene encodes an enzyme selected from the group consisting of pyruvate decarboxylase pdc 1 designated SPAC 1 F8.07 serine protease isp 6 designated SPAC4A8.04; and
transforming the *Schizosaccharomyces pombe* yeast cell with a polynucleotide which encodes the heterologous protein,
wherein the deletion or inactivation of the at least one gene results in increased production of the heterologous protein compared to a *Schizosaccharomyces pombe* yeast cell in which the at least one gene has not been deleted or inactivated;
culturing the yeast cell constructed such that the heterologous protein is produced by the yeast cell; and collecting the heterologous protein.

* * * * *